(12) United States Patent
Tong et al.

(10) Patent No.: US 10,722,745 B2
(45) Date of Patent: Jul. 28, 2020

(54) INTERACTIVE CYCLING SYSTEM AND METHOD OF USING MUSCLE SIGNALS TO CONTROL CYCLING PATTERN STIMULATION INTENSITY

(71) Applicant: The Chinese University of Hong Kong, Hong Kong (CN)

(72) Inventors: Kai Yu Tong, Hong Kong (CN); Wing Cheong Leung, Hong Kong (CN); Xiao Jun Wang, Hong Kong (CN); Sai Chen, Hong Kong (CN); Yu Qi Fang, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 218 days.

(21) Appl. No.: 16/000,181

(22) Filed: Jun. 5, 2018

(65) Prior Publication Data
US 2019/0366146 A1 Dec. 5, 2019

(51) Int. Cl.
*A63B 21/00* (2006.01)
*A63B 22/06* (2006.01)
(Continued)

(52) U.S. Cl.
CPC ...... *A63B 21/00181* (2013.01); *A61B 5/0488* (2013.01); *A61F 5/0116* (2013.01); *A61N 1/0452* (2013.01); *A61N 1/0476* (2013.01); *A61N 1/36003* (2013.01); *A61N 1/36031* (2017.08); *A63B 21/0058* (2013.01); *A63B 21/4034* (2015.10); *A63B 22/0694* (2013.01); *A63B 24/0062* (2013.01); *A63B 24/0087* (2013.01); *A61B 2505/09* (2013.01);
(Continued)

(58) Field of Classification Search
CPC ............... A61N 1/0452; A61N 1/0476; A61N 1/36003; A61N 1/36031; A61N 1/36014; A61N 1/0492; A61F 5/0116; A63B 21/00181; A63B 22/0694; A63B 24/0062; A63B 24/0087; A63B 21/0058; A63B 21/4034; A63B 2220/30; A63B 2022/0635; A63B 2024/0093; A63B 2230/085; A63B 2230/605; A63B 2213/004; A63B 2022/0094; A63B 2220/836; A61B 5/0488; A61B 2505/09; A61B 5/6891
See application file for complete search history.

(56) References Cited

U.S. PATENT DOCUMENTS 5,016,635 A 5/1991 Graupe
8,923,978 B1 * 12/2014 Hartman ............ A61N 1/36003
607/48
(Continued)

*Primary Examiner* — Sundhara M Ganesan
(74) *Attorney, Agent, or Firm* — Saliwanchik, Lloyd & Eisenschenk

(57) ABSTRACT

Systems and methods for a muscle signal-driven cycling system for persons with disability for rehabilitation are provided. A system comprises integrating both motor power and muscle power to facilitate rehabilitation cycling-based exercises. By using the intensity of real-time muscle activity signals as inputs, a motor applies either assistive or resistive force to rotate a gear at different speeds to facilitate or impede the cycling motion, and the electrical pulses from an electrical stimulation device can be provided to stimulate target muscles to generate muscle contraction to support the continuous cycling movement.

22 Claims, 22 Drawing Sheets

(51) Int. Cl.
   *A63B 24/00*      (2006.01)
   *A61B 5/0488*     (2006.01)
   *A61N 1/04*       (2006.01)
   *A61F 5/01*       (2006.01)
   *A61N 1/36*       (2006.01)
   *A63B 21/005*     (2006.01)
   *A63B 22/00*      (2006.01)

(52) U.S. Cl.
   CPC ............ *A63B 2022/0094* (2013.01); *A63B 2022/0635* (2013.01); *A63B 2024/0093* (2013.01); *A63B 2213/004* (2013.01); *A63B 2220/30* (2013.01); *A63B 2220/836* (2013.01); *A63B 2230/085* (2013.01); *A63B 2230/605* (2013.01)

(56) References Cited

U.S. PATENT DOCUMENTS

| | | | |
|---|---|---|---|
| 2004/0259693 A1* | 12/2004 | Chien | A61H 1/0214 |
| | | | 482/62 |
| 2005/0209049 A1* | 9/2005 | Shields | A61H 1/001 |
| | | | 482/8 |
| 2006/0247095 A1 | 11/2006 | Rummerfield | |
| 2007/0208392 A1* | 9/2007 | Kuschner | A61N 1/36003 |
| | | | 607/48 |
| 2009/0326607 A1 | 12/2009 | Castel et al. | |
| 2017/0100586 A1* | 4/2017 | Akiba | A61N 1/36 |
| 2018/0056061 A1* | 3/2018 | Nishimura | A61N 1/36003 |

\* cited by examiner

INTERACTIVE CYCLING SYSTEM AND METHOD OF USING MUSCLE SIGNALS TO CONTROL CYCLING PATTERN STIMULATION INTENSITY

BACKGROUND

Stationary bicycles can be used as tools for rehabilitation by individuals who have suffered from a stroke or lower limb disability. Recovery from an injury can be enhanced by stimulation of target muscles during treatment. The system described herein strengthens muscles, bone, and muscle coordination.

BRIEF SUMMARY

Embodiments of the subject invention provide a muscle signal-driven cycling system for rehabilitation for persons with disability. The bikes can be used by individuals who have suffered from a stroke or a lower limb disability in both home-based and clinical settings. The system is intended to strengthen their muscles, bone, and muscle coordination.

The system can integrate both motor power and muscle power in order to facilitate a rehabilitative exercise. By using the intensity of muscle signals as the inputs for a voluntary intention (muscle activities from surface electrodes), the motor can be driven to rotate at different speeds to facilitate a cycling motion. Electrical pulses from a stimulator can stimulate the target muscles to generate muscle contraction to support a continuous cycling motion. The interactive cycling system can also leverage external power to facilitate unilateral leg training without the involvement of the unaffected leg.

DETAILED DESCRIPTION

The muscle signal-driven cycling rehabilitation system can be used by individuals who have suffered from disabilities including a stroke or a lower limb disability.

Figure 1A:
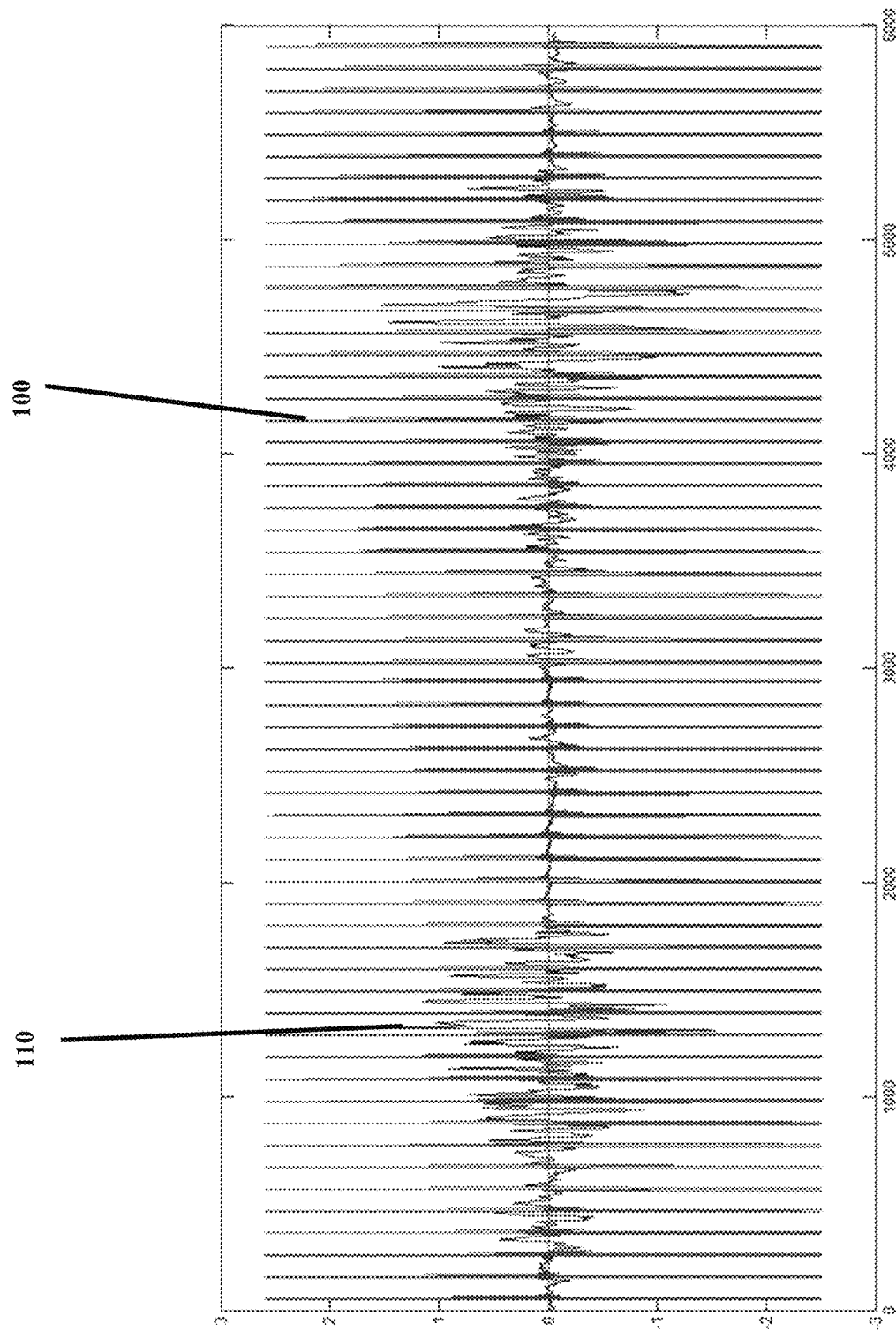
FIG. 1a is a plot of a processed muscle signal using electromyography (EMG) that includes a stimulation artifact signal.
Figure 1B:
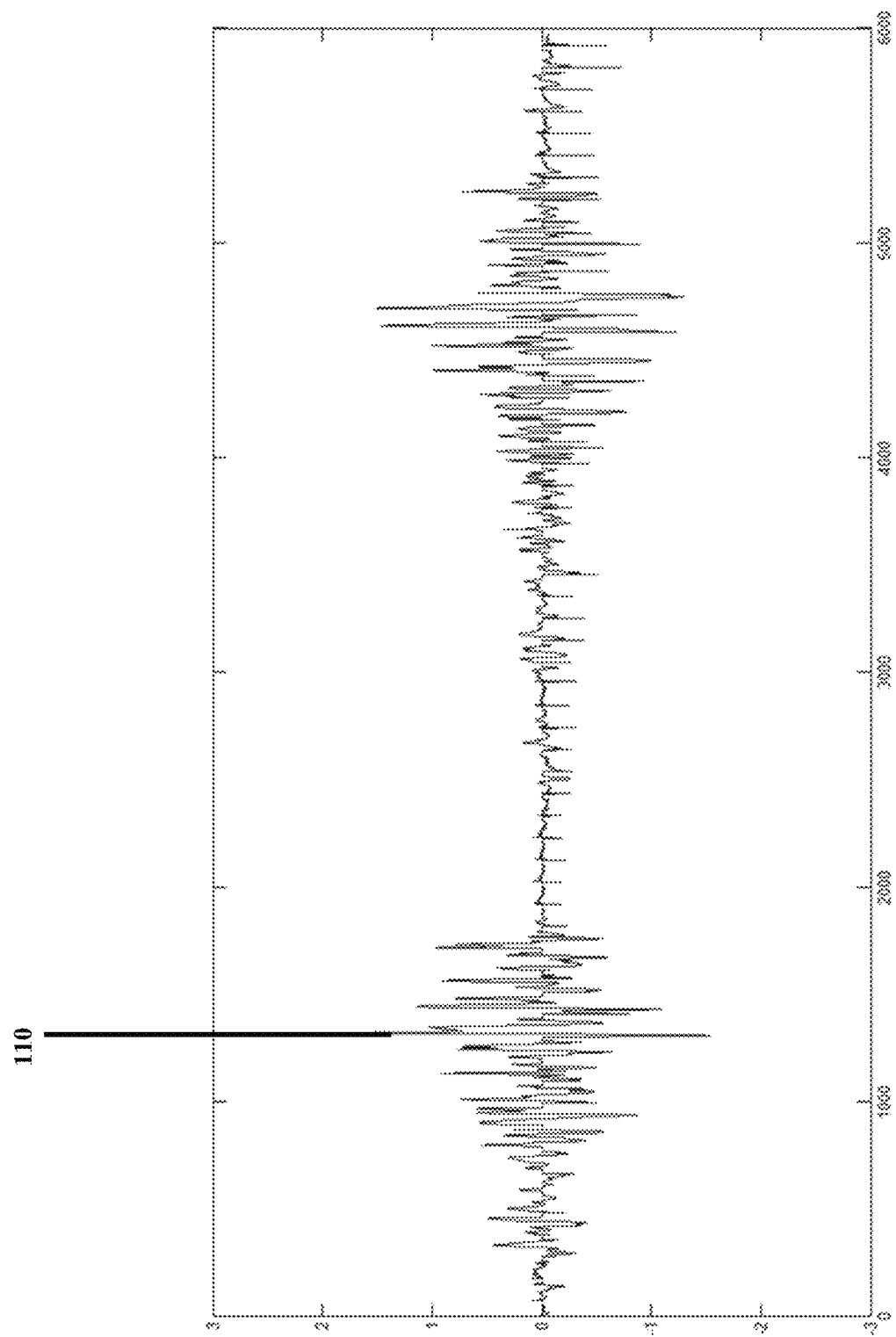
FIG. 1b is a plot of the processed muscle signal excluding the stimulation artifact signal.
Figure 1C:
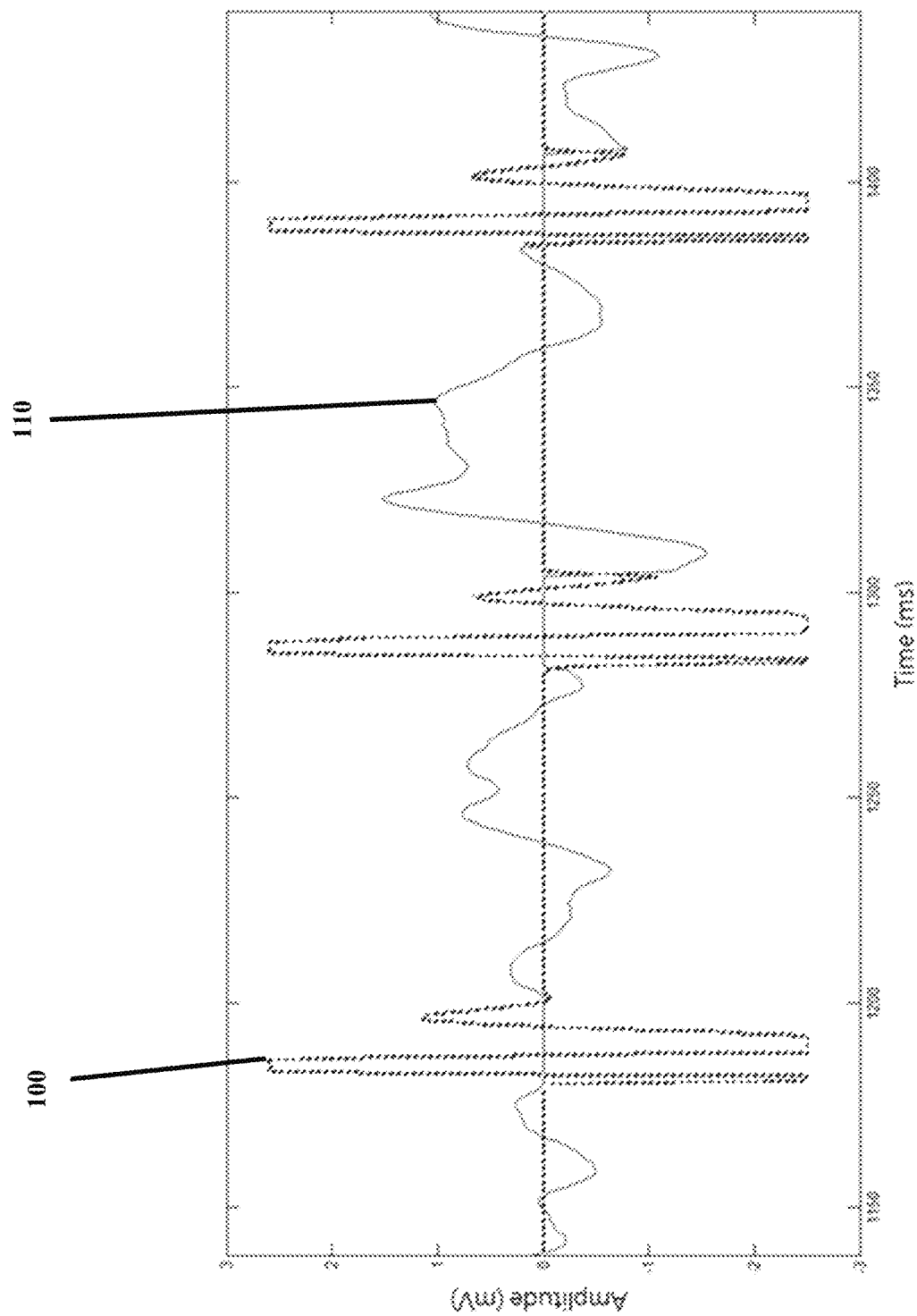
FIG. 1c is a zoomed-in plot of the processed muscle signal and the stimulation artifact signal.
Figure 2:
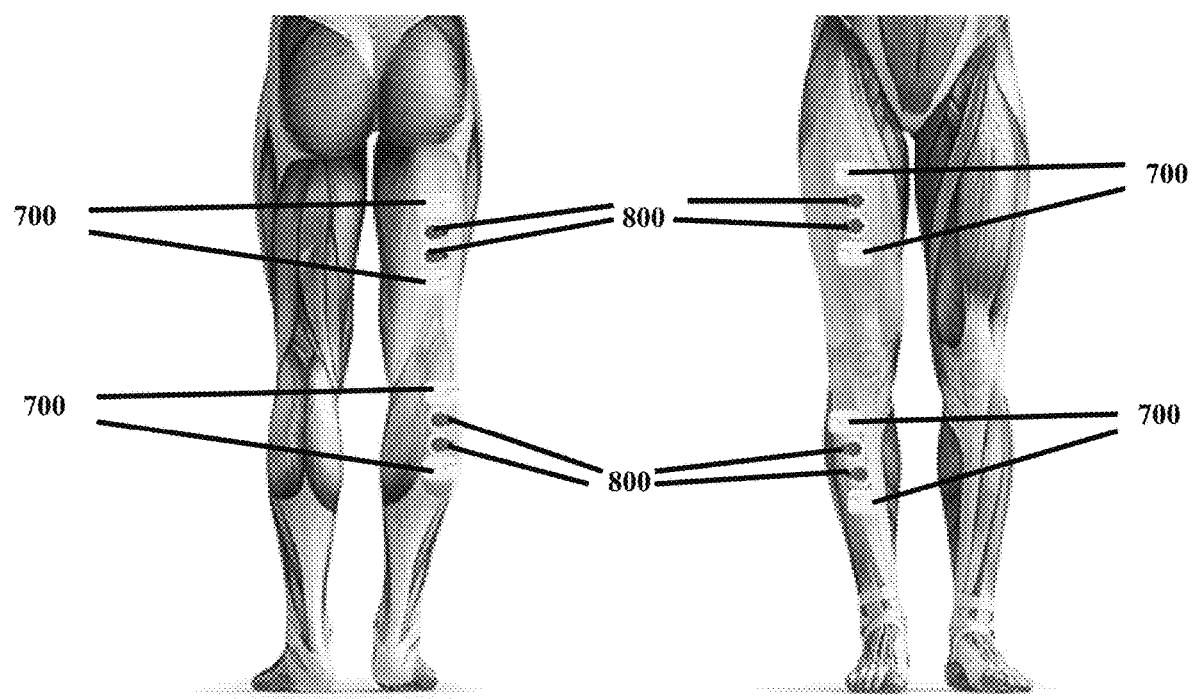
FIG. 2 is a diagram of the muscular system of the legs with electrical stimulation electrodes and EMG electrodes placed on the hamstrings, quadriceps, gastrocnemius, and tibialis anterior muscles.

FIG. 2 is a diagram illustrating the placement of four pairs of electrical stimulation electrodes 700 and surface electromyography (EMG) electrodes 800 on the leg muscles of a subject in need of rehabilitation. Multiple surface EMG electrodes 800 can be positioned on a user's quadriceps, hamstrings, gastrocnemius, and tibialis anterior muscles. The surface EMG electrodes comprise a non-invasive array of electrodes that can be adhered to target locations of the body. The EMG electrodes 800 are used to measure the electrical potential difference between the electrodes 800. The interactive cycling system can collect muscle signals responsive to the user's leg movements during cycling in order to adjust the cycling speed and stimulation intensity to improve rehabilitation. Although FIGS. 2, 10, and 11 display one pair of surface EMG electrodes 800 on each muscle, the interactive cycling system can be configured to include more EMG electrodes 800 on each muscle or use intramuscular EMG electrodes. The muscle signals can be collected by using surface EMG electrodes, needle EMG electrodes, ultrasound sensors, or vibration sensors.

Electrical stimulation electrodes 700 can be paired with the EMG electrodes 800 on the user's quadriceps, hamstrings, gastrocnemius, and tibialis anterior muscles. The electrical stimulation electrodes receive stimulation signals from a stimulator and transmit electrical impulses to the user's muscles. The interactive cycling systems can increase or decrease the stimulation signal intensity based upon the pattern of muscle signals collected from the target muscles. The stimulation signal intensity can be adjusted to provide continuous interactive assistance towards the user's leg movements while the user is cycling. The interactive cycling system can continuously collect muscle signals responsive to the user's leg movement in order to continuously adjust the stimulation signal intensity to assist rehabilitation (for example, to improve stroke rehabilitation).

Figure 3:
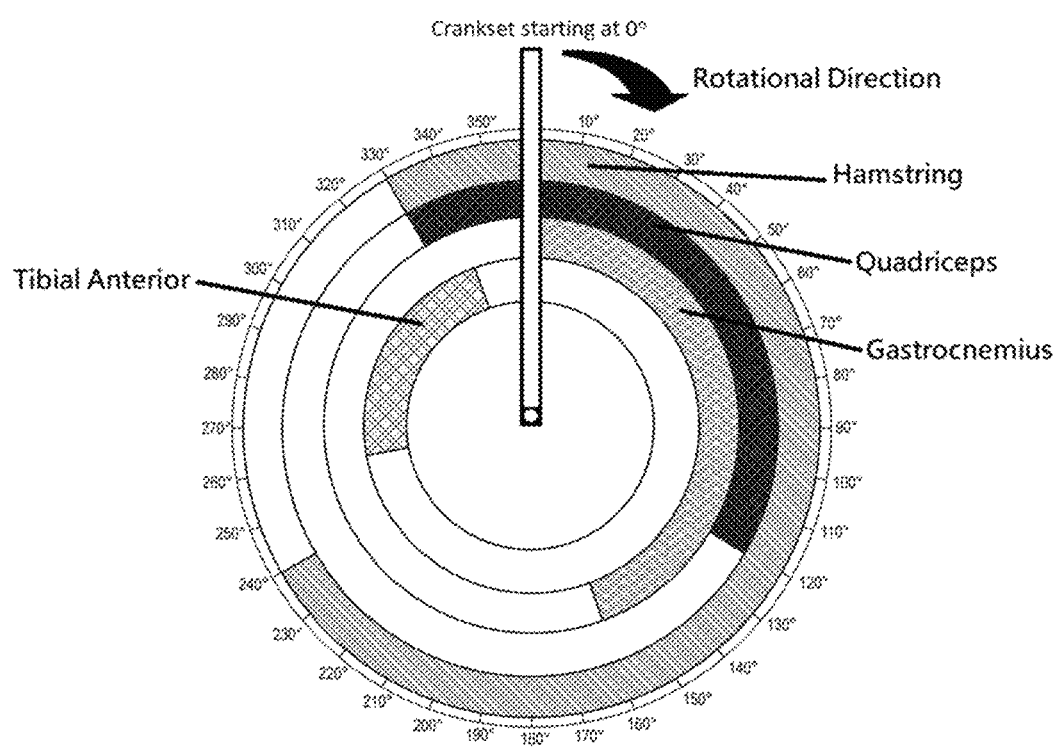
FIG. 3 is a diagram illustrating the cycling pattern as it relates to the hamstrings, quadriceps, gastrocnemius, and tibialis anterior muscles.

FIG. 3 illustrates an example of a cycling stimulation pattern for each target muscle group. 0° is defined as where both crank arms 920 are vertical and the affected leg is extended. The system can be configured to provide stimulation signals to target locations of the user's legs based upon the position of the crank arm 920 across a rotational angle arc. Each target muscle group has a cycling stimulation pattern comprised of a specific angle arc. For example, the hamstring muscle has a cycling stimulation pattern 300 between 330°-240°. The quadriceps muscle has a cycling stimulation pattern 310 between 330°-120°, the gastrocnemius muscle has a cycling stimulation pattern 320 between 0°-160°, and the tibialis anterior muscle has a cycling stimulation pattern 330 between 260°-340°. Table 1 summarizes the different stimulation patterns for each of the target muscle groups.

TABLE 1

Leg Motions During Cycling

| Crank Angle | Muscle Stimulated | Lower Extremity Motion |
| --- | --- | --- |
| 330°-240° | Hamstring | Knee Flexion |
| 330°-120° | Quadriceps | Knee Extension |
| 0°-160° | Gastrocnemius | Ankle Plantarflexion |
| 260°-340° | Tibialis Anterior | Ankle Dorsiflexion |

Figure 4:
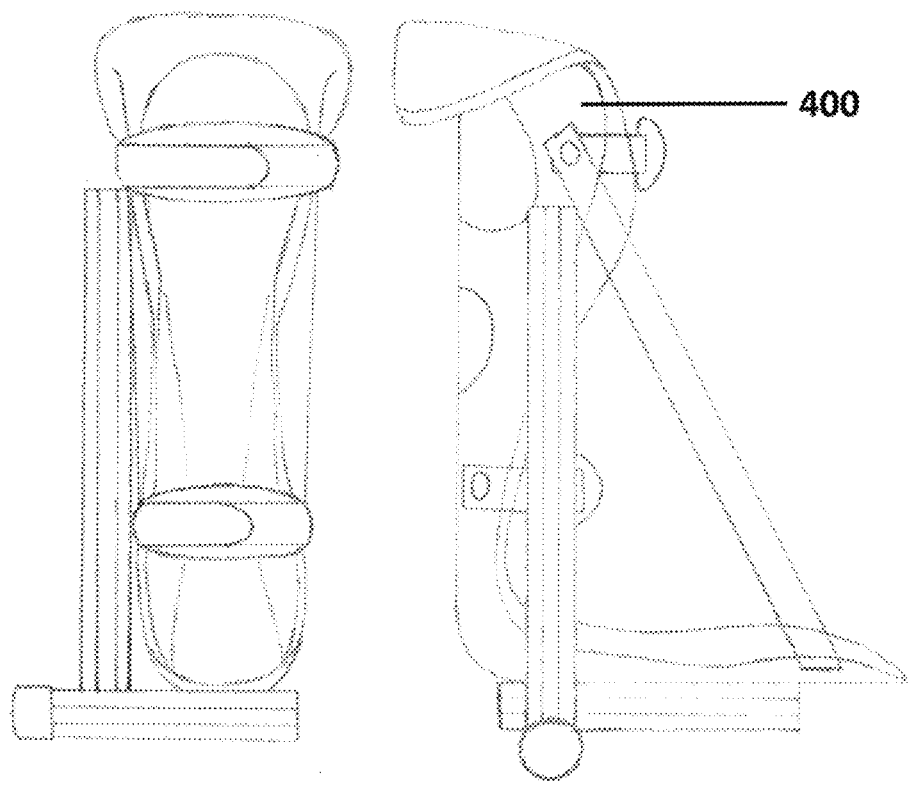
FIG. 4 is an image of the front view (left) and side view (right) of the ankle orthosis with an L-shaped profile.

The front view and a side view of the ankle orthoses that can be worn by a user of the interactive cycling system can be seen in FIG. 4. The ankle orthoses 400 can have an L-shaped profile and can be configured to allow the user's legs to remain in a sagittal plane, keep the angle-knee-hip joints aligned with the pedal, and inhibit hip abduction in order to optimize the forward driving force during cycling.

Figure 5A:
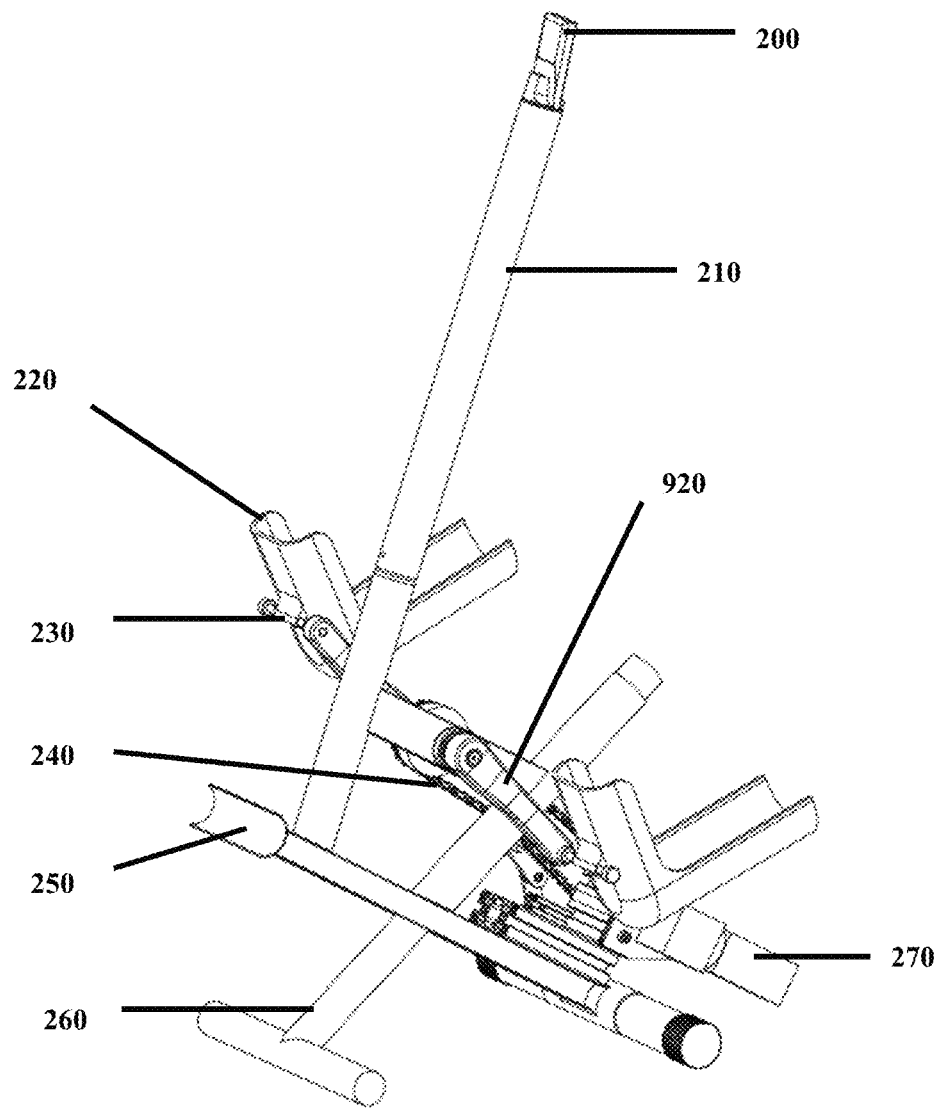
FIG. 5a is a diagram of the interactive cycling system from a 450 angle.
Figure 5B:
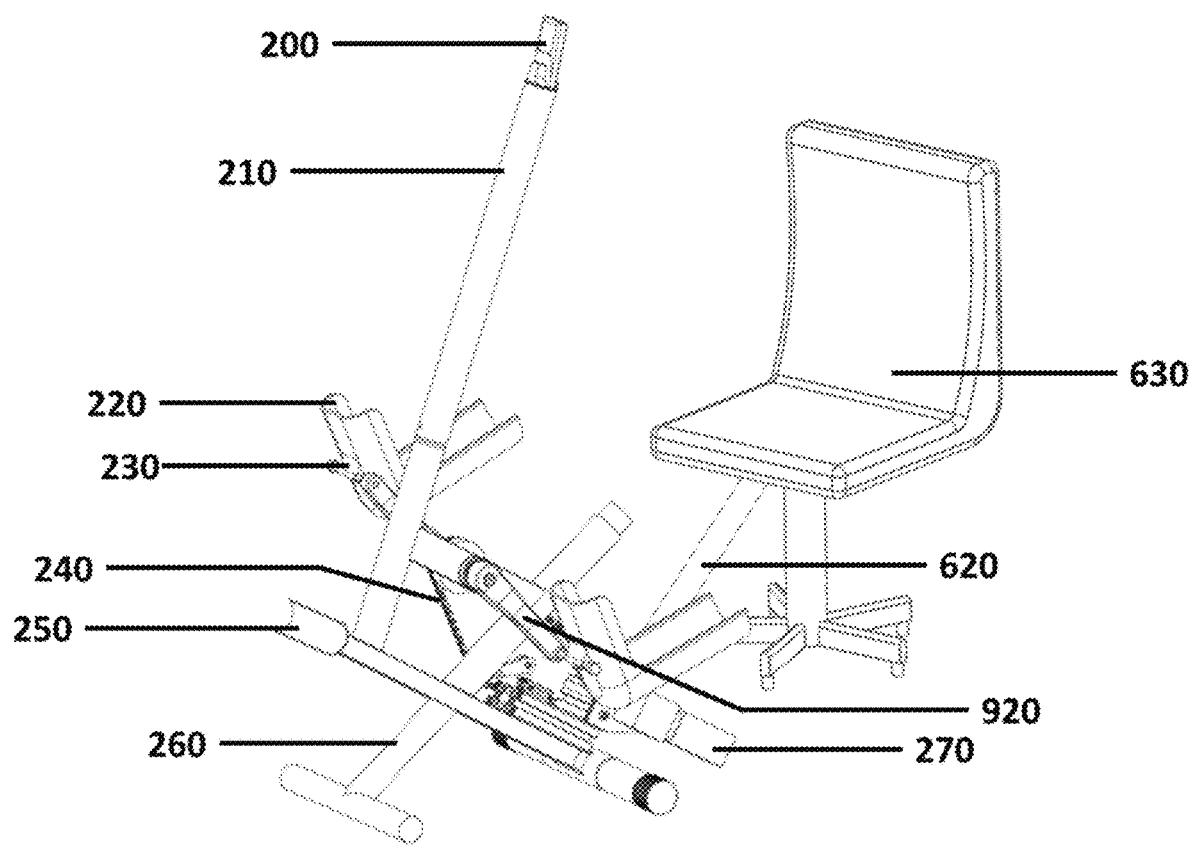
FIG. 5b is an image of the interactive cycling system from a 450 angle.

As seen in FIGS. 5a and 5b, the interactive system comprises a display 200 connected to a connection bar 210, a pedal 220 connected to a respective crank arm 920 to optimize the forward force during cycling, and a force sensor 230 connected to each pedal. The force sensor can be a three-axial sensor and comprise a piezoresistive 3-D force sensor or CMOS-based force sensor. The connection bar can be connected to a base bar 250 and a stand bar 260 to provide support during operation of the interactive cycling system. The interactive cycling system is equipped with a motor 270 connected to the rear gear of the cycle. The motor 270 can provide assistive or resistive force in response to the intensity of the EMG signal from a user's muscle. Although FIGS. 5a and 5b display a rear hub motor 270, the interactive cycling system can be configured to include a centrally located motor or otherwise be connected to the drive chain 240 to generate the pedaling force. In an embodiment of the subject invention the interactive cycling system can be equipped with an extendable chair adaptor 620 for users who require wheelchairs 630, as seen in FIG. 5b.

Figure 6A:
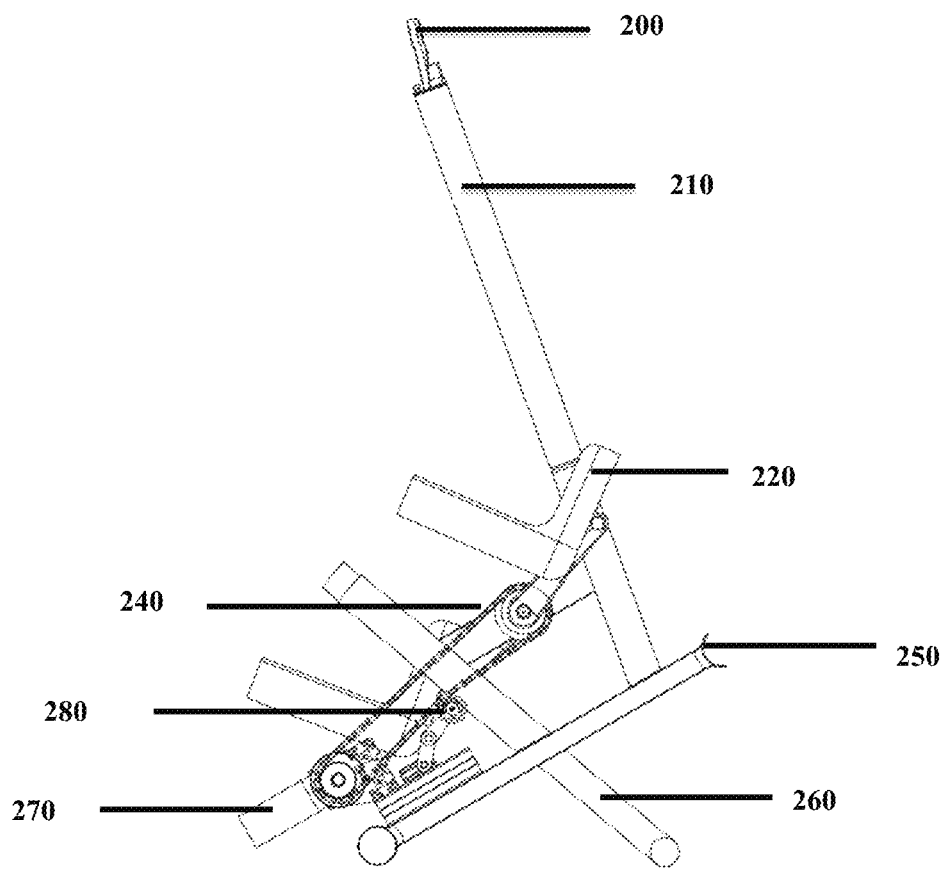
FIG. 6a is a diagram of one side of the interactive cycling system from a 900 angle.
Figure 6B:
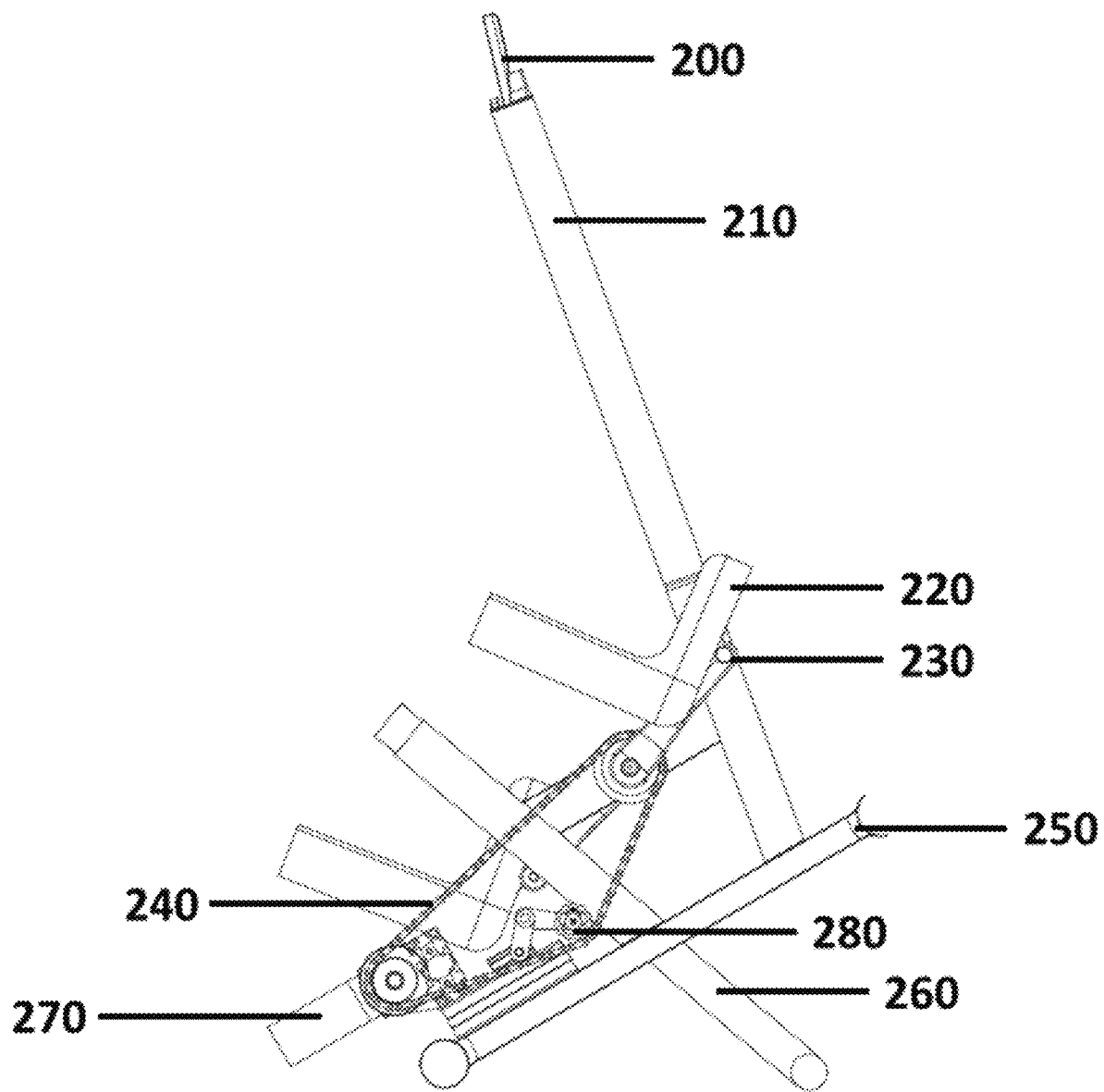
FIG. 6b is an image of one side of the interactive cycling system from a 900 angle.

FIGS. 6a and 6b are a diagram and an image of a side view of the interactive cycling system. The system can include a tensioner 280 to create or maintain tension to inhibit slack from developing in the chain 240.

Figure 7:
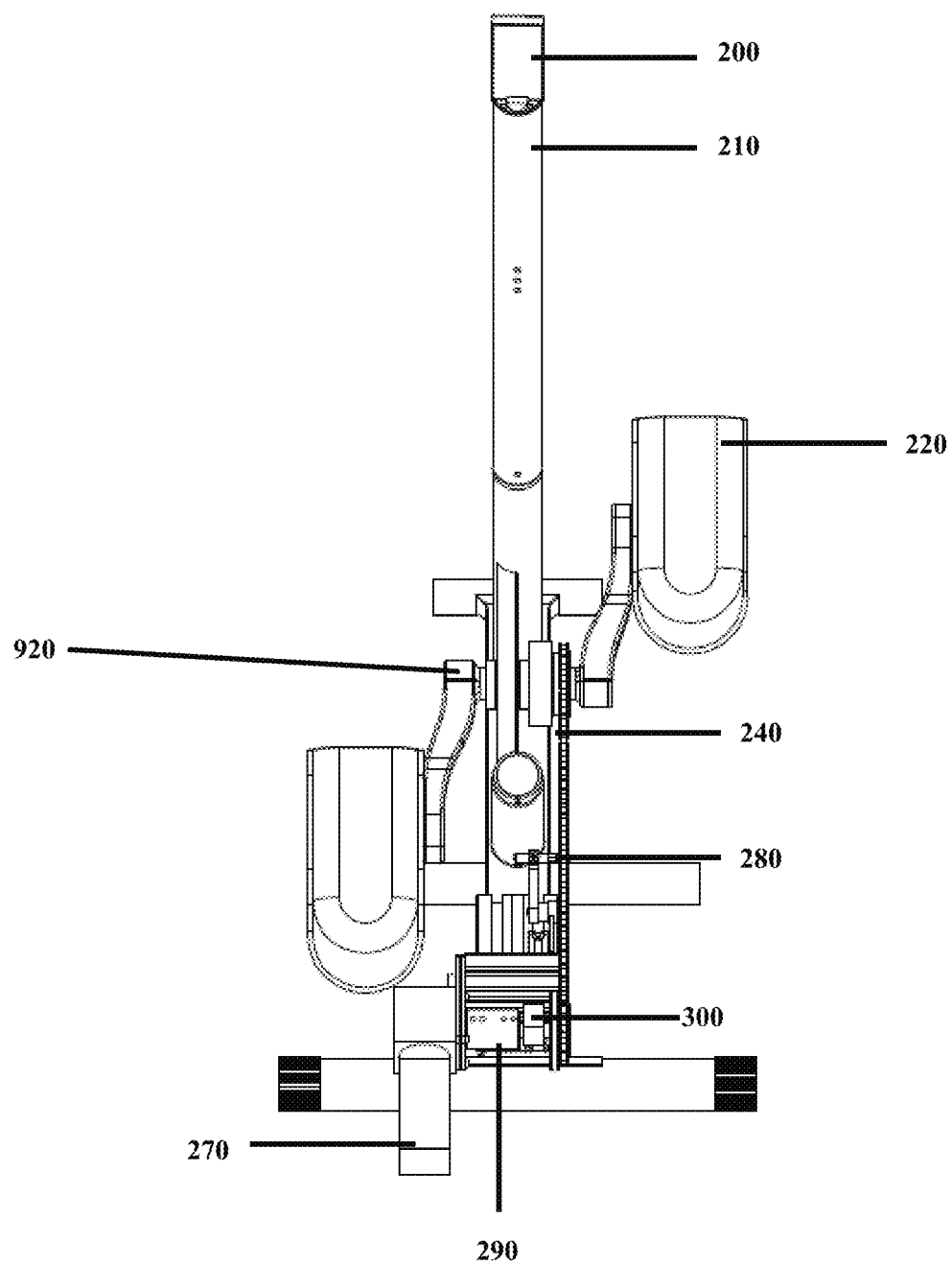
FIG. 7 is a diagram of the rear view of the interactive cycling system.
Figure 8:
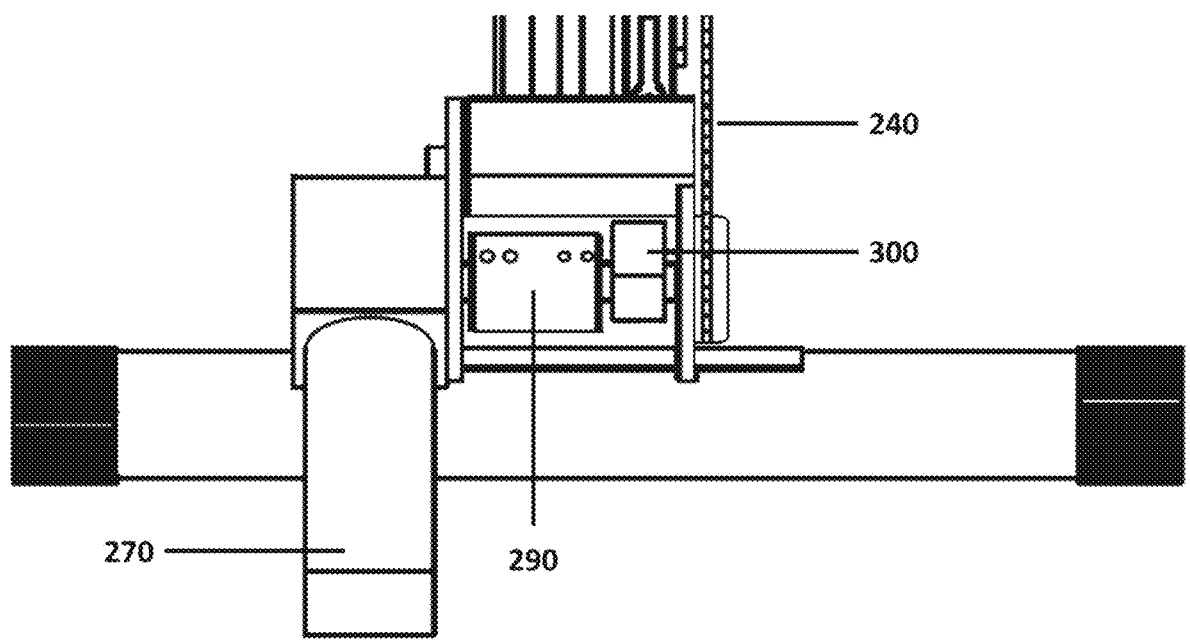
FIG. 8 is an image showing the motor coupling torque sensor of the interactive cycling system.
Figure 9:
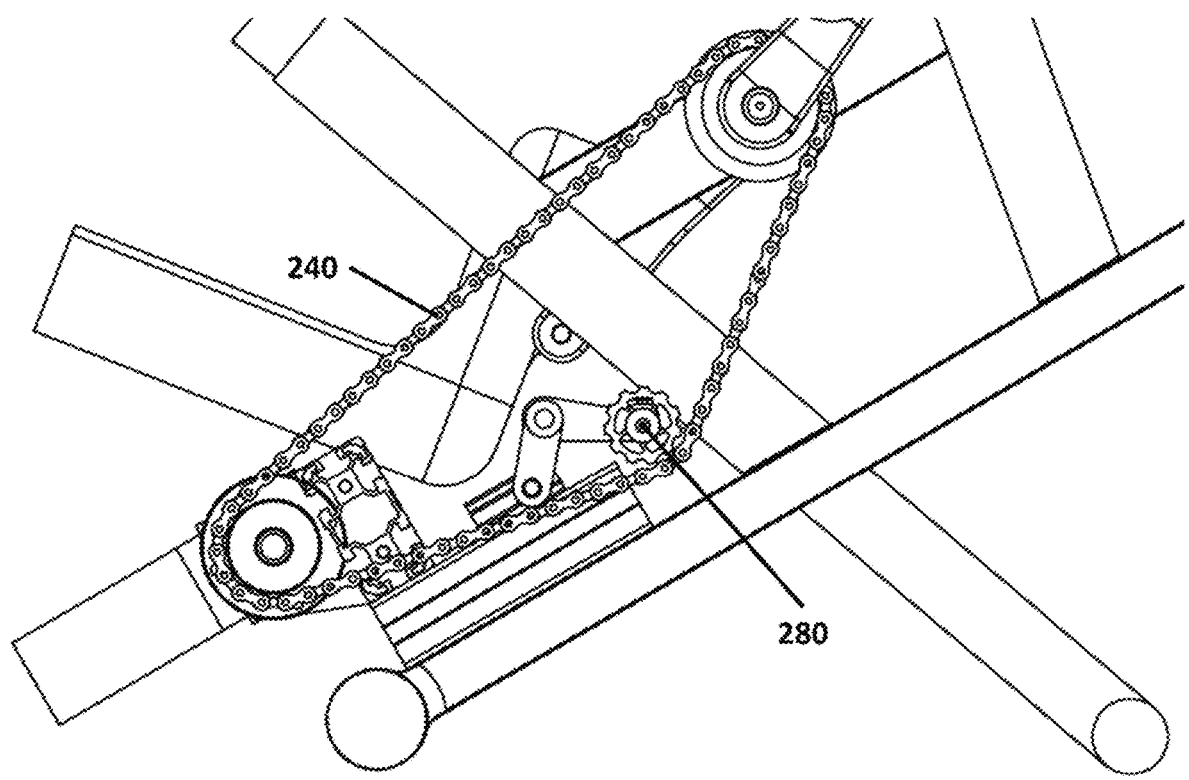
FIG. 9 is an image showing the chain drive configuration of the interactive cycling system.

FIGS. 7 and 8 are a diagram and image of the rear of the interactive cycling system. The motor 270 can be connected to a torque sensor 300 through a coupling connector 290. The torque sensor 300 is a transducer that measures the torque from the mechanical force provided by the user to the pedal and converts the mechanical input to an electronic signal. The measurement of the torque allows the system to determine the magnitude of the assistive or resistive force to be applied by the motor 270. FIG. 9 is an image illustrating the tensioner 280 applying a variable mechanical force to the chain 240 to increase or reduce tension on the chain.

Figure 10:
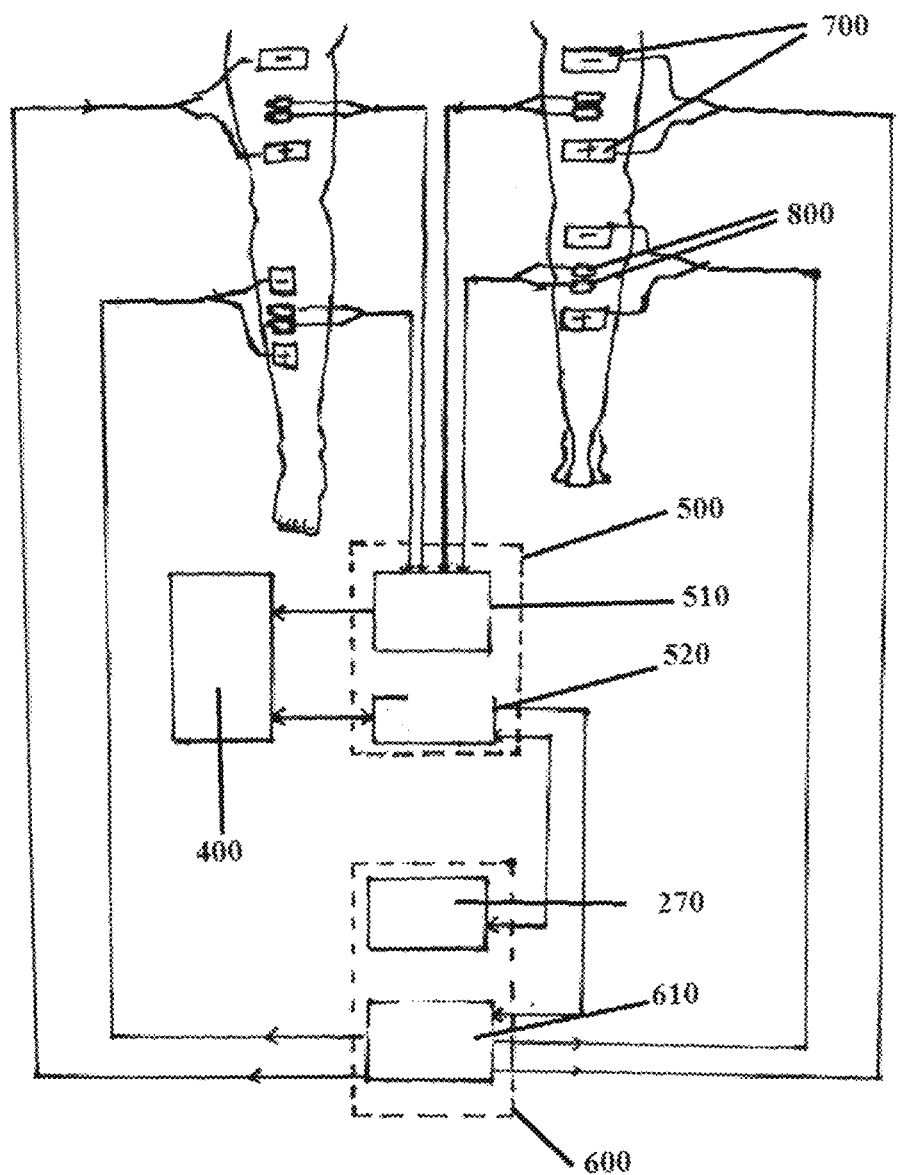
FIG. 10 is a diagram illustrating the configuration of the interactive cycling system, control box, and electrodes of the interactive cycling system.
Figure 11:
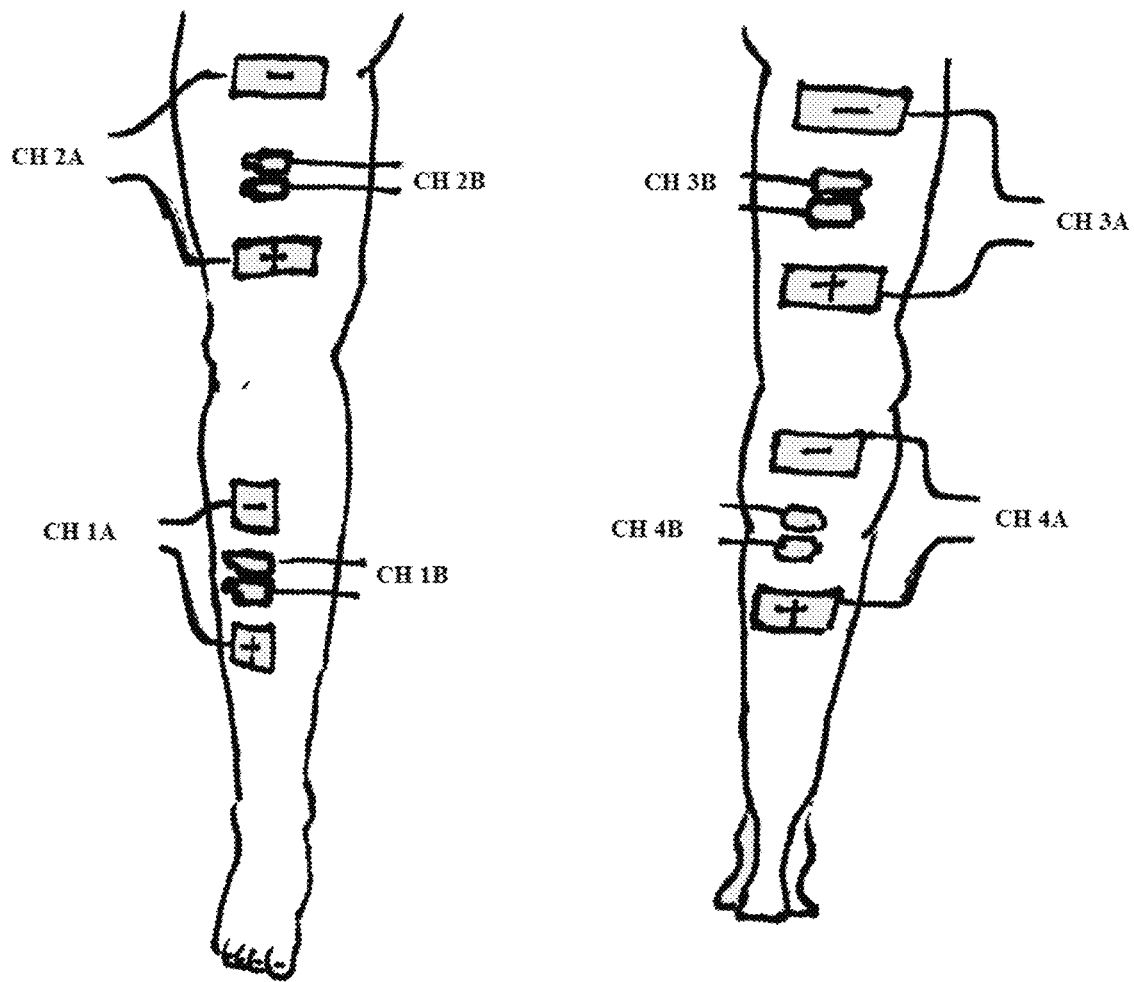
FIG. 11 is a diagram illustrating the electrical stimulation electrodes and EMG electrodes placement on the hamstrings, quadriceps, gastrocnemius, and tibialis anterior muscles.

FIGS. 10 and 11 are diagrams of the interactive cycling system. The electrical stimulation electrodes 700 can be adhered to the skin of a user and provide an interface to transmit electrical stimulation signals from the stimulator 610 through four channels CH 1A, CH 2A, CH 3A, and CH 4A in response to movement of target muscles. EMG electrodes 800 can be adhered to the user's skin and be positioned on a user's hamstrings, quadriceps, gastrocnemius, or tibialis anterior muscles. The EMG electrodes 800 can continuously collect and provide real time muscle signals through the four channels CH 1B, CH 2B, CH 3B, and CH4 band and transmit the data to control mechanism 500. The control mechanism 500 can include a data acquisition system 510 and a controller 520. The control mechanism 500 can be in electronic communication with a computing device 400 comprising a central processing unit, a display, a graphics processing unit, peripheral devices, a mouse, a keyboard, and memory.

In an embodiment of the subject invention a processor 400 can be used to implement the control algorithm. The processor 400 can be equipped with on-off capabilities, an EMG amplifier with a filter, and motor control (for example UIRobot UIM24104). Additionally, the system is capable of collecting EMG signals at, for example, a 5 KHz sampling frequency and store the information in memory (for example an SD card).

A portable four-channel programmable stimulator 610 can provide real time control of the system based upon the control algorithm in order to generate different stimulation patterns. The stimulator 610 can provide a stimulation frequency in a range between 0 Hz and 50 Hz, a pulse bandwidth between 100 μs and 500 μs, and an adjustable intensity between 0 and 100 mA. The stimulator 610 can be portable with dimensions of 15 cm×8 cm×2.5 cm and be light weight (400 g).

The processor 400 can be in electronic communication with a controller 520 to interface with the interactive cycling system 600. Amplified muscle signals can be collected by a data acquisition (DAQ) device 510 from a user's muscles to drive the stimulation patterns of the stimulator 610 through the controller 520 (for example solid state relay with an Arduino™ development board). Real time crank angles can be simultaneously collected to generate a cycling pattern on each muscle group, the stimulation pulses are generated by the stimulator 610 to stimulate the contraction of the quadriceps, hamstrings, gastrocnemius, and tibialis anterior muscles through surface electrodes 700, thereby creating continuous cycling movement. Based upon the recorded muscle signals the processor can direct the motor 270 to change the cycling speed by providing either a resistive or an assistive force.

Figure 12A:
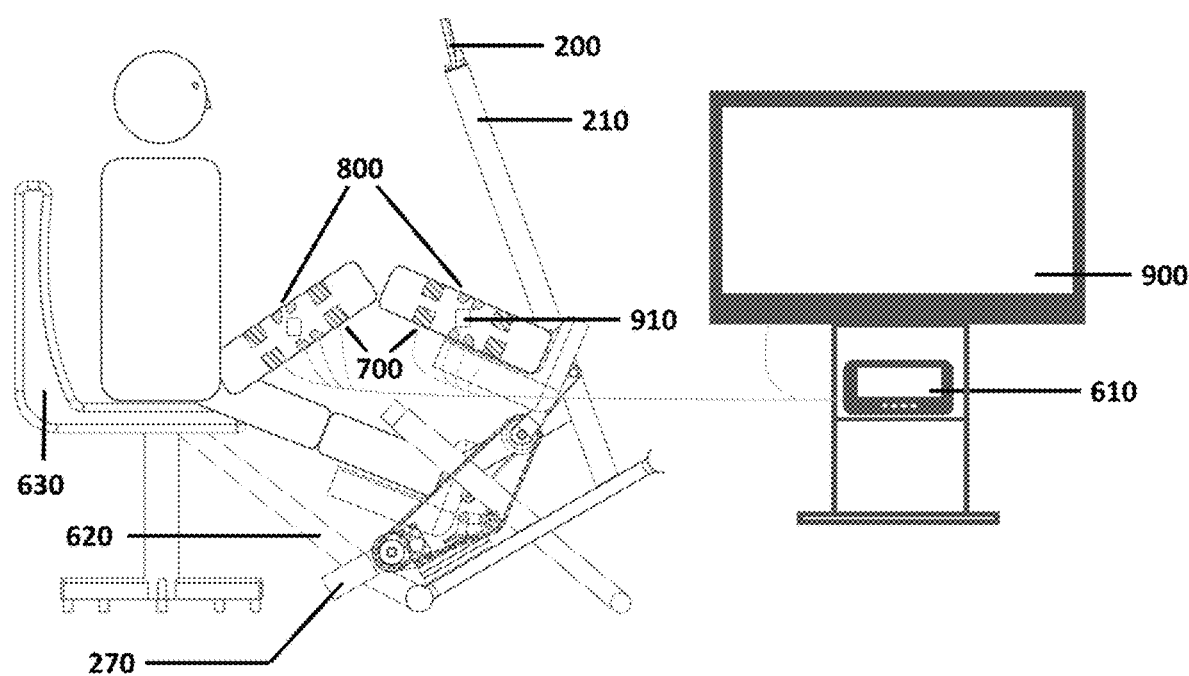
FIG. 12a is an image of the interactive cycling system with unilateral training.
Figure 12B:
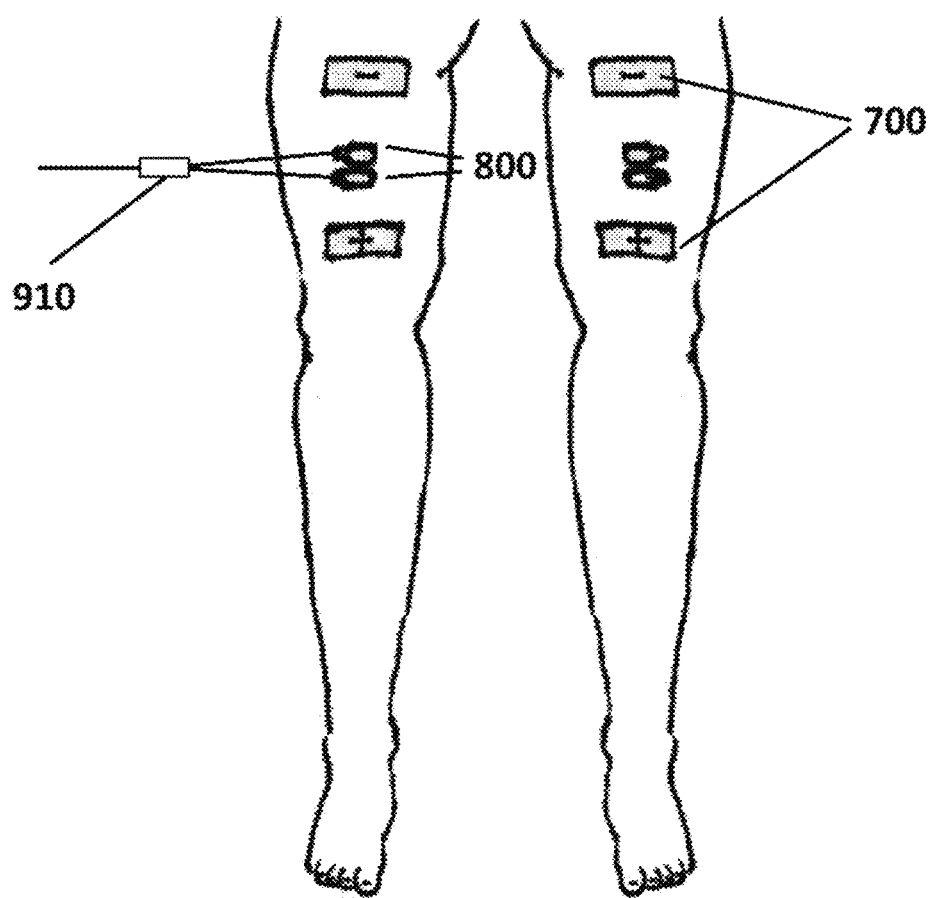
FIG. 12b is an image of the interactive cycling system with bilateral leg training.

FIGS. 12a and 12b are images of a user operating the interactive cycling system with unilateral and bilateral leg training, respectively. The system can be configured to provide external power from a motor and/or electrical stimulation signals to facilitate both unilateral and bilateral leg training. The EMG electrodes 800 can be connected to an EMG amplifier 910 to amplify the muscle signals generated from the user's muscles. The user can be positioned to monitor the signal responses and stimulation signal intensities though a display 900 connected to the processor 400.

Figure 13:
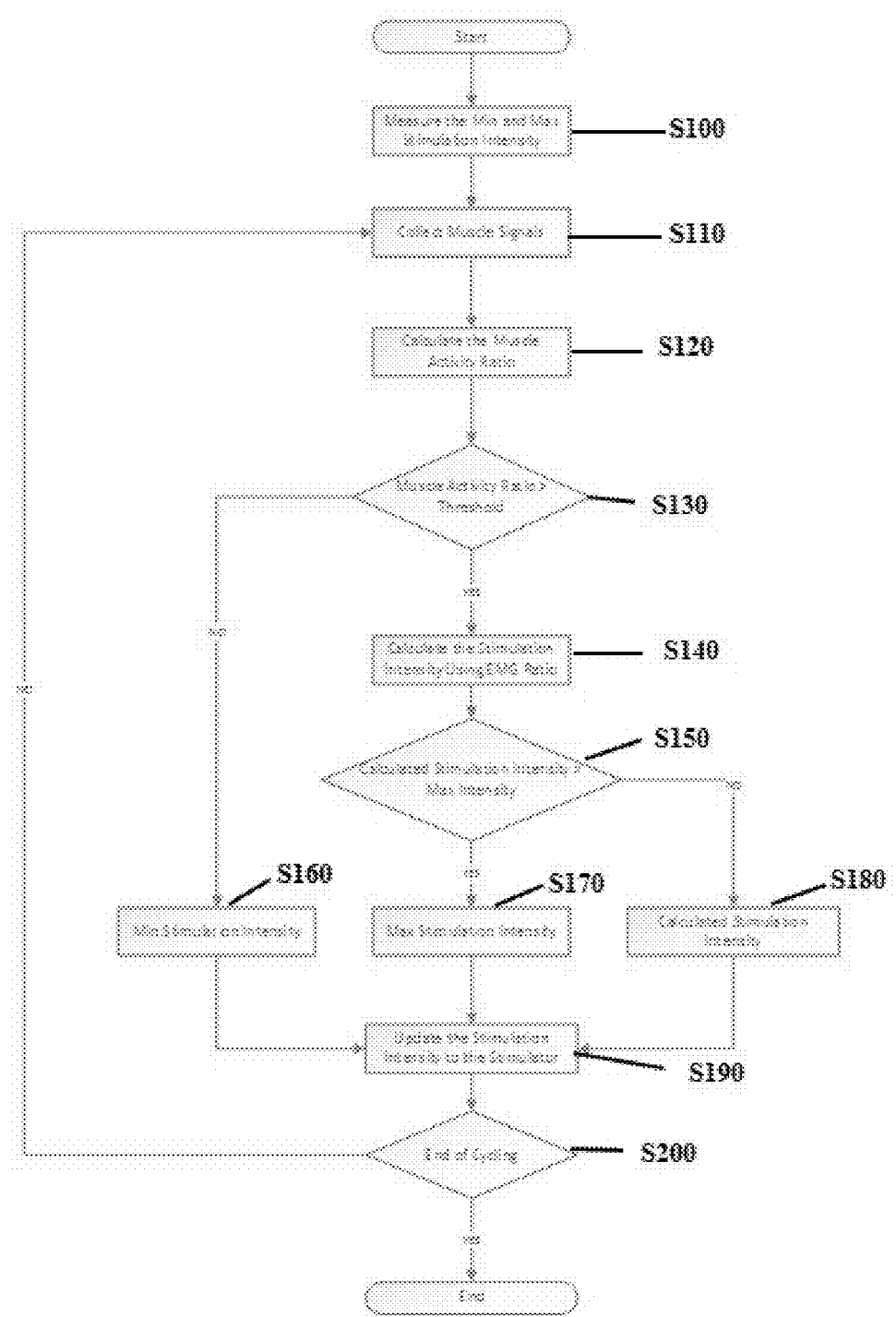
FIG. 13 is a flow chart illustrating the process for determining electrical stimulation intensity.

FIG. 13 is a flow chart describing a method to continuously determine the stimulation signal intensity. A first step can be to determine each response of target muscles of a user to different signal intensities S100 to determine a minimum and a maximum stimulation intensity of a user. A second step can be to collect muscle signals S110 from target muscles of the user. The recorded muscle signals can be amplified, filtered, and stored in memory for analysis. A third step can be to calculate the ratio of the amplitude of the muscle activation ratio S120. If the muscle activation ratio is less than a threshold value S130, the system can deliver S190 the minimum stimulation signal intensity S160. If, however, the muscle activation ratio is greater than a threshold value S130, the stimulation signal intensity can be calculated using the muscle activation ratio S140. If the calculated stimulation signal intensity is greater than the maximum stimulation signal intensity S150, as determined in the first step, the system can update the stimulator to deliver S190 a stimulation signal equal to the maximum intensity S170. If the calculated stimulation signal intensity is less than the maximum intensity, the system can update the NMES device to deliver S190 a stimulation signal equivalent to the calculated stimulation signal intensity S180. The processer can keep collecting muscle signals and repeat itself until the user quits cycling S200.

Figure 14:
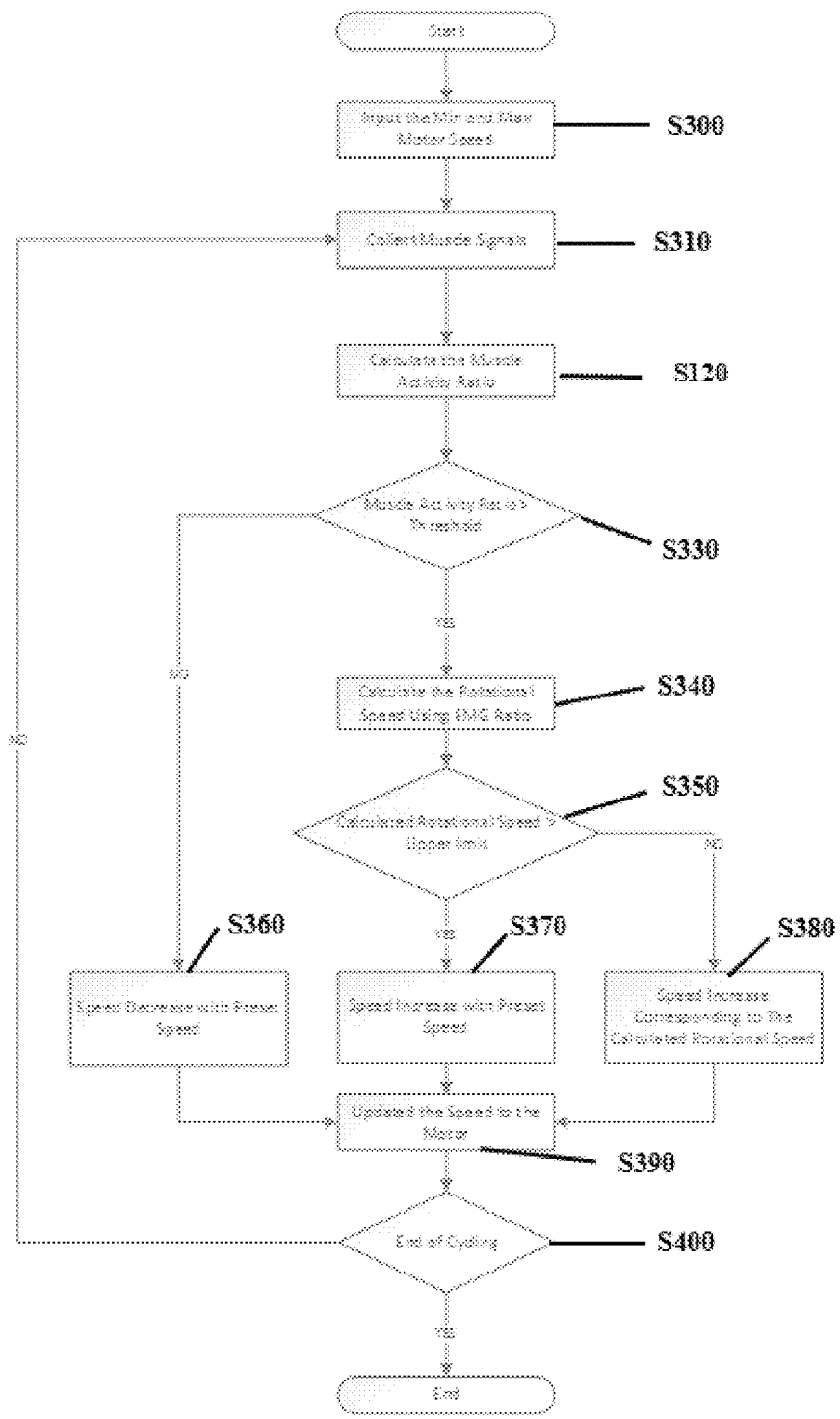
FIG. 14 is a flow chart illustrating the process for determining proper motor speed.

FIG. 14 is a flow chart describing a method to continuously determine the assistive or resistive force applied by the motor. A first step can be to input a minimum and maximum motor speed S300. A second step can be to collect muscle signals S310 from target muscles of the user. The recorded muscle signals can be amplified, filtered, and stored in memory for analysis. The muscle signal can be transmitted to the processor, which can calculate the muscle activation ratio S120. If the muscle activation ratio is less than a threshold value S330, the processor can direct the motor S390 to generate a resistive force to slow down the user's peddling rate S360. If, however, the muscle activation ratio is greater than the threshold value S330, the desired rotational speed can be calculated using the muscle activation ratio S340 and an upper limit S350, the motor S390 can adjust the rotational speed to a preset speed S370. If the calculated rotational speed is less than the upper limit, the motor S390 can adjust the rotational speed to correspond to the calculated rotational speed S380, but limited to a range of an inputted minimum and maximum motor speed S300. The processor can keep collecting muscle signals and repeating itself until the user quits cycling S400.

The first method of calculating the muscle activation ratio S120 corresponds to the percentage of overlap of an activation time window 510 between the real-time muscle activity pattern and the desired muscle activity pattern. A larger overlap value represents a better matching with the desired muscle activity pattern. The range of the percentage of overlap can be from 0 to 100%.

The second method of calculating the muscle activation ratio S120 is dependent upon the muscle signal amplitude. A large amplitude corresponds to a large force generated from muscles. A user needs to generate sufficient voluntary force from their muscle to control the stimulation signal intensity and motor speed of the system.

Figure 15A:
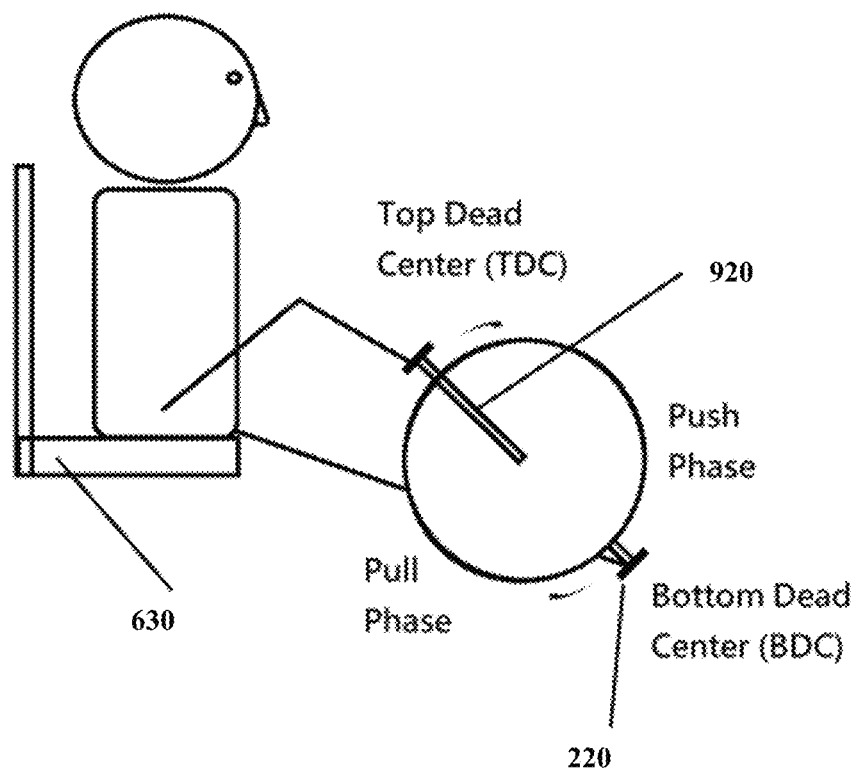
FIG. 15a is a diagram illustrating the interactive cycling system in a recumbent posture design.
Figure 15B:
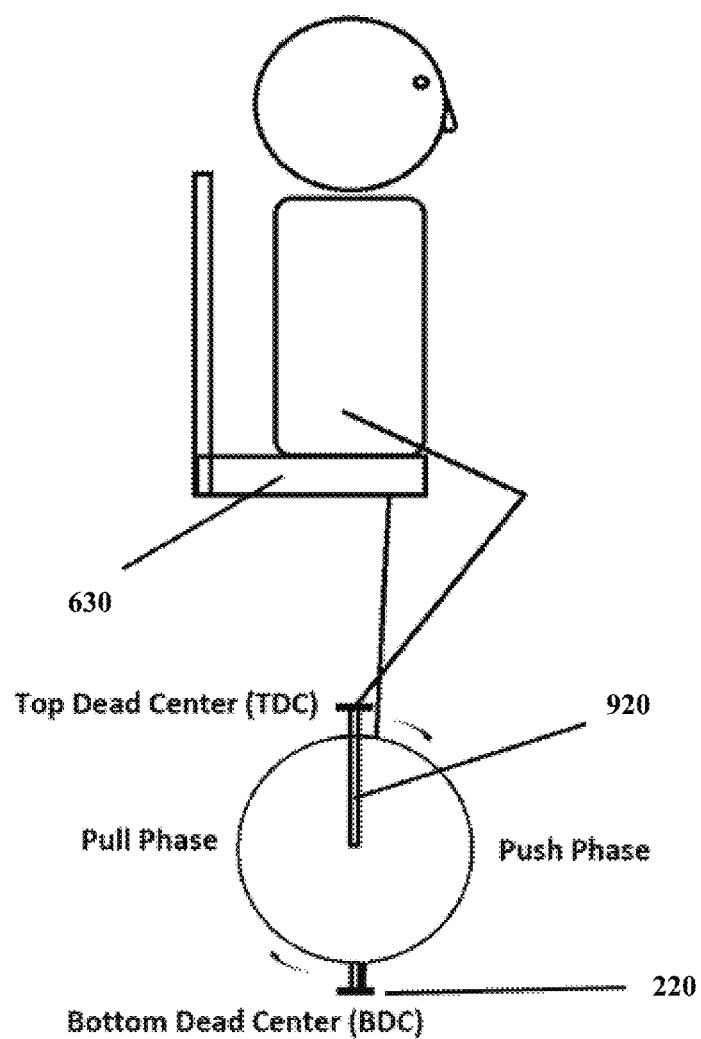
FIG. 15b is a diagram illustrating the interactive cycling system in an upright posture design.

FIGS. 15a and 15b are diagrams identifying a push phase, in which the force is generated to push the pedal forward from top dead center (TDC) to bottom dead center (BDC), and a pull phase, in which the force is generated to pull the pedal backward from BDC to TDC of the interactive cycling system in both a recumbent and an upright posture design.

Figure 16:
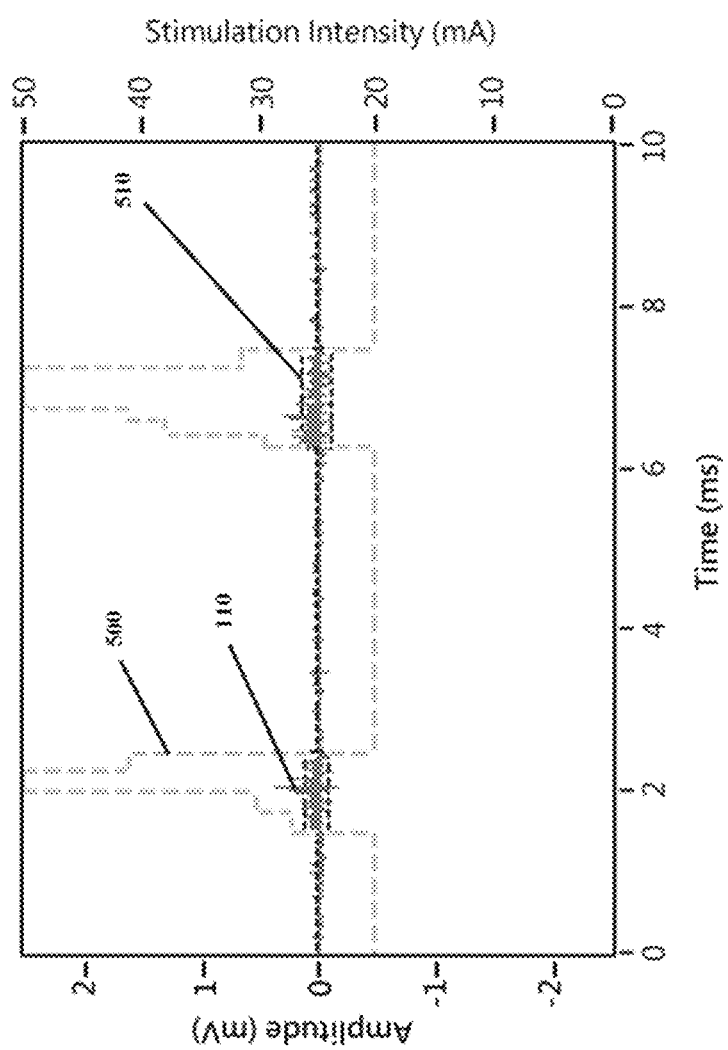
FIG. 16 is a diagram of a processed muscle signal that is 100% overlapped with an activation time window.

FIG. 16 is a diagram of a processed muscle signal 110 that is 100% overlapped with the activation time window 510. The stimulation signal intensity 500 is shown and corresponds to the muscle signal amplitude.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processer reads and executes the code and/or data stored on a computer-readable medium, the computer system and/or processer performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

The subject invention includes, but is not limited to, the following exemplified embodiments.

Embodiment 1

A system for using muscle signals to control a cycling pattern, the system comprising:

a pedal;

a crank arm connected to the pedal;

a motor connected to the crank arm;

a stimulator connected to a plurality of stimulation electrodes;

a controller connected to the motor and the stimulator; and a data acquisition system connected to the controller and a muscle activity sensor, wherein the motor is configured to apply either an assistive force or a resistive force to the crank arm, wherein the stimulator is configured to transmit a stimulation signal across the plurality of stimulation electrodes, wherein the data acquisition system is configured to continuously receive a muscle signal, wherein the controller is configured to direct the motor to apply either the assistive force or the resistive force based upon the muscle signal, and wherein the controller is configured to direct the stimulator to increase or decrease an intensity of a stimulation signal based upon the muscle signal.

Embodiment 2

The system of embodiment 1, wherein the pedal is affixed to an ankle orthosis with an L-shaped profile.

Embodiment 3

The system according to any of embodiments 1-2, wherein a force sensor is connected to the pedal.

Embodiment 4

The system according to any of embodiments 1-3, wherein a force sensor is connected to the crank arm.

Embodiment 5

The system according to any of embodiments 1-4, wherein a front gear is connected to the crank arm.

Embodiment 6

The system of embodiment 5, wherein a chain is mechanically connected to the front gear and a rear gear.

Embodiment 7

The system of embodiment 6, wherein a torque sensor is connected to the rear gear.

Embodiment 8

The system of embodiment 7, wherein the torque sensor is further connected to the motor and the controller.

Embodiment 9

The system according to any of embodiments 1-8, wherein the muscle activity sensor and the plurality stimulation electrodes are configured to be connected to a single leg to train an affected leg movement without the involvement of an unaffected leg.

Embodiment 10

The system according to any of embodiments 1-8, wherein the muscle activity sensor and the plurality stimulation electrodes are configured to be connected to both the left leg and right leg to train a lower limb movement.

Embodiment 11

The system according to any of embodiments 1-10, wherein the muscle activity sensor and a pair of stimulation electrodes are configured to be electrically connected to a hamstring muscle of a user.

Embodiment 12

The system according to any of embodiments 1-11, wherein the muscle activity sensor and a pair of stimulation electrodes are configured to be electrically connected to a quadriceps muscle of a user.

Embodiment 13

The system according to any of embodiments 1-12, wherein the muscle activity sensor and a pair of stimulation electrodes are configured to be electrically connected to a gastrocnemius muscle of a user.

Embodiment 14

The system according to any of embodiments 1-13, wherein the muscle activity sensor and a pair of stimulation electrodes are configured to be electrically connected to a tibialis anterior muscle of a user.

Embodiment 15

The system according to any of embodiments 1-14, wherein the stimulator is configured to stimulate a hamstring muscle of a user by emitting a stimulation signal when a rotational angle of the crank arm changes as the hamstring muscle contracts.

Embodiment 16

The system according to any of embodiments 1-15, wherein the stimulator is configured to stimulate a quadriceps muscle of a user by emitting a stimulation signal when a rotational angle of the crank arm changes as the quadriceps muscle contracts.

Embodiment 17

The system according to any of embodiments 1-16, wherein the stimulator is configured to stimulate a gastrocnemius muscle of a user by emitting a stimulation signal when a rotational angle of the crank arm changes as the gastrocnemius muscle contracts.

Embodiment 18

The system according to any of embodiments 1-17, wherein the stimulator is configured to stimulate a tibialis anterior muscle of a user by emitting a stimulation signal when a rotational angle of the crank arm is change as the tibialis anterior muscle contracts.

Embodiment 19

A method for using muscle signals to control a stimulation signal intensity during a cycling operation, the method comprising:
providing a computer readable medium to a system as described in embodiment 1,
wherein the computer readable medium comprising stored instructions that when executed cause at least one processor to:
determine each respective response of a user to different respective intensities of a stimulation signal to determine a minimum and maximum stimulation signal intensity while the user is cycling;
collect a muscle signal from a target muscle of the user while the user is cycling;
determine whether a muscle activation ratio is greater than or less than a threshold value;
direct a stimulator of the system to transmit a stimulation signal to the target muscle,
wherein the intensity of the stimulation signal is dependent upon whether the muscle activation ratio is greater than the threshold value; and
repeat the method until the user stops cycling.

Embodiment 20

The method of embodiment 19, wherein the muscle activation ratio is determined to be less than the threshold value and the stored instructions further cause the processor to:

direct the stimulator to transmit a stimulation signal having the minimum intensity to the target muscle.

Embodiment 21

The method of embodiment 19, wherein the muscle activation ratio is determined to be greater than the threshold value and the stored instructions further cause the processor to:

calculate a desired stimulation signal intensity based upon the muscle activation ratio;

determine whether the calculated desired stimulation signal intensity is greater than or less than the maximum stimulation signal intensity; and direct the stimulator to transmit a rehabilitative stimulation signal to the target muscle, wherein the intensity of the stimulation signal is dependent upon whether the calculated desired stimulation signal intensity is greater than the maximum stimulation signal intensity.

Embodiment 22

The method of embodiment 21, wherein the calculated desired stimulation signal intensity is determined to be greater than the maximum stimulation signal intensity and the stored instructions further cause the processor to:

direct the stimulator to transmit a rehabilitative stimulation signal having the maximum stimulation intensity to the target muscle.

Embodiment 23

The method of embodiment 21, wherein the calculated desired stimulation signal intensity is determined to be less than the maximum stimulation signal intensity and the stored instructions further cause the processor to:

direct the stimulator to transmit a rehabilitative stimulation signal having the calculated desired stimulation signal intensity to the target muscle.

Embodiment 24

The method of embodiment 19, wherein the stored instructions further cause the processor to:

calculate the muscle activation ratio from a percentage of overlap of an activation time window between a real-time muscle activity pattern and a desired muscle activity pattern; or calculate the muscle activation ratio from an actual amplitude of the real-time muscle signal and a desired amplitude of the real-time muscle signal.

Embodiment 25

A method for using muscle signals to control a force applied by a motor to a pedal during a cycling operation, the method comprising:

providing a computer readable medium to a system as described in embodiment 1, wherein the computer readable medium comprises stored instructions that when executed cause at least one processor to:

determine a minimum and a maximum rotational speed of a crank arm of the system while the user is cycling;

collect a muscle signal from a target muscle of the user while the user is cycling;

determine whether a muscle activation ratio is greater than or less than a threshold value;

direct the motor of the system to apply an assistive force or a resistive force; and repeat the method until the user stops cycling.

Embodiment 26

The method of embodiment 25, wherein the muscle activation ratio is determined to be less than the threshold value and the stored instructions further cause the processor to:

direct the motor of the system to apply a resistive force to decrease a rotational speed of the crank arm of the system to correspond with a preset speed.

Embodiment 27

The method of embodiment 25, wherein the muscle activation ratio is determined to be greater than the threshold value and the stored instructions further cause the processor to:

calculate a desired rotational speed of the crank arm of the system based upon the muscle activation ratio;

determine whether the calculated desired rotational speed is greater than or less than an upper limit; and direct the motor to apply an assistive force based upon whether the calculated desired rotational speed of the crank arm of the system is greater than the upper limit.

Embodiment 28

The method of embodiment 27, wherein the calculated desired rotational speed of the crank arm is determined to be greater than the upper limit and the stored instructions further cause the processor to:

direct the motor of the system to apply an assistive force to the pedal of the system to increase the rotational speed of the crank arm of the system to a preset speed.

Embodiment 29

The method of embodiment 27, wherein the calculated desired rotational speed is determined to be less than the upper limit and the stored instructions further cause the processor to:

direct the motor of the system to apply an assistive force to increase the rotational speed of the crank arm of the system to correspond to the calculated desired rotational speed.

Embodiment 30

The method of embodiment 25, wherein the stored instructions further cause the processor to:

calculate the muscle activation ratio from a percentage of overlap of an activation time window between a real-time muscle activity pattern and a desired muscle activity pattern; or calculate the muscle activation ratio from an actual amplitude of a real-time muscle signal and a desired amplitude of the real-time muscle signal.

Example 1

A stationary bike (X2FIT-HG-599-17A), was equipped with an extendable chair adapter for wheelchair users and a subject was seated in a modified standard chair. A motor producing a 15 Nm torque and 50 rpm was mounted on the metal frame. According to the intensity of the EMG signal from the lower limb muscle of the user, the torque of the motor changes in order to provide either an assistive or a resistive force during the cycling exercise. This design is suitable for individuals who have suffered from a stroke or lower limb disability for the training on the affected leg. The unaffected leg can rest on the side without being involved in the training.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

What is claimed is:

1. A system for using muscle signals to control a cycling pattern, the system comprising:
    a pedal;
    a crank arm connected to the pedal;
    a motor connected to the crank arm;
    a stimulator connected to a plurality of stimulation electrodes;
    a controller connected to the motor and the stimulator; and
    a data acquisition system connected to the controller and a muscle activity sensor;
    wherein the motor is configured to apply either an assistive force or a resistive force to the crank arm,
    wherein the stimulator is configured to connect to the plurality of stimulation electrodes and transmit a stimulation signal,
    wherein the data acquisition system is configured to receive a real-time muscle signal,
    wherein the controller is configured to direct the motor to apply either the assistive force or the resistive force based upon the real-time muscle signal, and
    wherein the controller is configured to direct the stimulator to increase or decrease an intensity of the stimulation signal based upon the real-time muscle signal.

2. The system of claim 1, wherein the pedal is affixed to an ankle orthosis with an L-shaped profile.

3. The system of claim 1, further comprising:
    a force sensor connected to the pedal;
    a force sensor connected to the crank arm;
    a front gear connected to the crank arm;
    a rear gear connected to the front gear by a chain; and
    a torque sensor connected to the rear gear, the motor, and the controller.

4. The system of claim 1, wherein for unilateral leg training the system is configured to attach a muscle sensor and stimulation electrodes to a single leg to train only that leg.

5. The system of claim 1, wherein for bilateral leg training the system is configured to attach muscle sensors and stimulation electrodes to both left and right legs.

6. The system of claim 1, wherein the muscle activity sensor and a pair of stimulation electrodes are configured to be attached to a hamstring muscle of a user, a quadriceps muscle of a user, a gastrocnemius muscle of a user, or a tibialis anterior muscle of a user.

7. The system of claim 1, wherein the stimulator is configured to stimulate a hamstring muscle of a user by emitting the stimulation signal when a rotational angle of the crank arm changes as the hamstring muscle contracts.

8. The system of claim 1, wherein the stimulator is configured to stimulate a quadriceps muscle of a user by emitting the stimulation signal when a rotational angle of the crank arm changes as the quadriceps muscle contracts.

9. The system of claim 1, wherein the stimulator is configured to stimulate a gastrocnemius muscle of a user by emitting the stimulation signal when a rotational angle of the crank arm changes as the gastrocnemius muscle contracts.

10. The system of claim 1, wherein the stimulator is configured to stimulate a tibialis anterior muscle of a user by emitting the stimulation signal when a rotational angle of the crank arm changes as the tibialis anterior muscle contracts.

11. A method for using muscle signals to control stimulation signal intensity during a cycling operation, the method comprising:
    providing a computer-readable medium to a system according to claim 1,
    wherein the computer-readable medium comprises stored instructions that when executed cause at least one processor to:
    sense, by a sensor, each respective response of a user to different respective intensities of a stimulation signal to determine a minimum and a maximum stimulation signal intensity while the user is cycling;
    sense, by a sensor, a muscle signal from a target muscle of the user while the user is cycling;
    determine whether a muscle activation ratio is greater than or less than a threshold value;
    direct a stimulator of the system to transmit a stimulation signal to the target muscle, intensity of the stimulation signal being dependent upon whether the muscle activation ratio is greater or lesser than the threshold value; and
    repeat the method until the user stops cycling.

12. The method of claim 11, wherein the muscle activation ratio is determined to be less than the threshold value and the stored instructions further cause the processor to:
    direct the stimulator to transmit a stimulation signal having the minimum stimulation signal intensity to the target muscle.

13. The method of claim 11, wherein the muscle activation ratio is determined to be greater than the threshold value and the stored instructions further cause the processor to:
    calculate a desired stimulation signal intensity based upon the muscle activation ratio;
    determine whether the calculated desired stimulation signal intensity is greater than or less than the maximum stimulation signal intensity; and
    direct the stimulator to transmit a stimulation signal to the target muscle,
    intensity of the stimulation signal being dependent upon whether the calculated desired stimulation signal intensity is greater than or less than the maximum stimulation signal intensity.

14. The method of claim 13, wherein the calculated desired stimulation signal intensity is determined to be greater than the maximum stimulation signal intensity and the stored instructions further cause the processor to:
  direct the stimulator to transmit a stimulation signal having the maximum stimulation intensity to the target muscle.

15. The method of claim 13, wherein the calculated desired stimulation signal intensity is determined to be less than the maximum stimulation signal intensity and the stored instructions further cause the processor to:
  direct the stimulator to transmit a stimulation signal having the calculated desired stimulation signal intensity to the target muscle.

16. The method of claim 11, wherein the stored instructions further cause the processor to:
  calculate the muscle activation ratio from a percentage of overlap of an activation time window between a real-time muscle activity pattern and a desired muscle activity pattern; or
  calculate the muscle activation ratio from an actual amplitude of a real-time muscle signal and a desired amplitude of the real-time muscle signal.

17. A method for using muscle signals to control a force applied by a motor during a cycling operation, the method comprising:
  providing a computer-readable medium to a system according to claim 1,
  wherein the computer-readable medium comprises stored instructions that when executed cause at least one processor to:
  determine a minimum and a maximum rotational speed of a crank arm of the system while a user is cycling;
  sense, by a sensor, a real-time muscle signal from a target muscle of the user while the user is cycling;
  determine whether a muscle activation ratio is greater than or less than a threshold value;
  direct the motor of the system to apply an assistive force or a resistive force; and
  repeat the method until the user stops cycling.

18. The method of claim 17, wherein the muscle activation ratio is determined to be less than the threshold value and the stored instructions further cause the processor to:
  direct the motor of the system to apply a resistive force to decrease a rotational speed of the crank arm of the system to correspond with a preset speed.

19. The method of claim 17, wherein the muscle activation ratio is deter mined to be greater than the threshold value and the stored instructions further cause the processor to:
  calculate a desired rotational speed of the crank arm of the system based upon the muscle activation ratio;
  determine whether the calculated desired rotational speed of the crank arm of the system is greater or lesser than an upper limit; and
  direct the motor of the system to apply an assistive force based upon whether the calculated desired rotational speed of the crank arm of the system is greater or lesser than the upper limit.

20. The method of claim 19, wherein whether the calculated desired rotational speed of the crank arm of the system is determined to be greater than the upper limit and the stored instructions further cause the processor to:
  direct the motor of the system to apply an assistive force to increase the rotational speed of the crank arm of the system to a preset speed.

21. The method of claim 19, wherein the calculated desired rotational speed of the crank arm of the system is determined to be less than the upper limit the stored instructions further cause the processor to:
  direct the motor of the system to apply an assistive force to increase the rotational speed of the crank arm of the system to correspond to the calculated desired rotational speed.

22. The method of claim 17, wherein the stored instructions further cause the processor to:
  calculate the muscle activation ratio from a percentage of overlap of activation time window between the real-time muscle activity pattern and the desired muscle activity pattern; or
calculate the muscle activation ratio from an actual amplitude of the real-time muscle signal and a desired amplitude of the real-time muscle signal.

* * * * *